US008106073B2

(12) United States Patent
Guile et al.

(10) Patent No.: US 8,106,073 B2
(45) Date of Patent: Jan. 31, 2012

(54) QUINOLINE DERIVATIVES 057

(75) Inventors: Simon David Guile, Loughborough (GB); Toby Thompson, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 508 days.

(21) Appl. No.: 12/324,397

(22) Filed: Nov. 26, 2008

(65) Prior Publication Data

US 2009/0143428 A1 Jun. 4, 2009

Related U.S. Application Data

(60) Provisional application No. 60/991,265, filed on Nov. 30, 2007.

(51) Int. Cl.
*A01N 43/42* (2006.01)
*C07D 215/44* (2006.01)

(52) U.S. Cl. ............... 514/313; 546/161; 546/281.4; 546/282.7; 546/284.1; 546/284.7; 546/337

(58) Field of Classification Search .................. 514/313
See application file for complete search history.

(56) References Cited

U.S. PATENT DOCUMENTS

| 3,464,998 | A | 9/1969 | Krimmel |
| 3,471,491 | A | 10/1969 | Venkatachala et al. |
| 4,751,292 | A | 6/1988 | Fox |
| 5,643,925 | A | 7/1997 | Naruto et al. |
| 5,804,588 | A | 9/1998 | Dyke et al. |
| 6,949,539 | B2 | 9/2005 | Alcaraz et al. |
| 7,129,246 | B2 | 10/2006 | Alcaraz et al. |
| 7,408,065 | B2 | 8/2008 | Evans et al. |
| 7,964,616 | B2 | 6/2011 | Guile et al. |
| 2001/0003121 | A1 | 6/2001 | Baxter et al. |
| 2004/0236109 | A1 | 11/2004 | Van Straten et al. |
| 2006/0293337 | A1 | 12/2006 | Evans et al. |
| 2008/0058293 | A1 | 3/2008 | Ford et al. |
| 2008/0058309 | A1 | 3/2008 | Cheshire et al. |
| 2008/0234319 | A1* | 9/2008 | Guile et al. .................. 514/314 |
| 2009/0143354 | A1 | 6/2009 | Evans et al. |
| 2009/0143428 | A1 | 6/2009 | Guile et al. |

FOREIGN PATENT DOCUMENTS

| BE | 650919 | 7/1964 |
| DE | 1943404 | 12/1970 |
| EP | 0002065 | 5/1979 |
| EP | 0501656 | 9/1992 |
| EP | 0867436 | 9/1998 |
| EP | 0940391 | 9/1999 |
| WO | WO95/04720 | 2/1995 |
| WO | WO97/19926 | 6/1997 |
| WO | WO99/26927 | 6/1999 |
| WO | WO99/29660 | 6/1999 |
| WO | WO99/29661 | 6/1999 |
| WO | WO00/61569 | 10/2000 |
| WO | WO00/73283 | 12/2000 |
| WO | WO01/37826 | 5/2001 |
| WO | WO01/94338 | 12/2001 |
| WO | WO03/042190 | 5/2003 |
| WO | WO03/045313 | 6/2003 |
| WO | WO03/080579 | 10/2003 |
| WO | WO03/087037 | 10/2003 |
| WO | WO2004/106305 | 12/2004 |
| WO | WO2005/009968 | 2/2005 |
| WO | WO2006/059945 | 6/2006 |

OTHER PUBLICATIONS

Muhl, H., Pfeilschifter, J., Interleukin-18 Bioactivity: a novel target for immunopharmacological anti-inflammatory intervention, 2004, European Journal of Pharmacology, 500, 63-71.*
Maerten, P., Shen, C., Colpaert, S., Liu, Z., Bullens, D., Van Assche, G., Penninckx, F., Geboes, K., Vanham, G., Rutgeerts, P., Ceuppens, J., Involvement of interleukin-18 in Crohn's disease: evidence from in vitro analysis of human gut inflammatory cells and from experimental colitis models, 2004, Clin Exp Immunol, 135, 310-317.*
Yamamura, M., Kawashima, M., Taniai, M., Yamauchi, H., Tanimoto, T., Kurimoto, M., Morita, Y., Ohmoto, Y., Makino, H., Interferon-γ-Inducing Activity of Interleukin-18 in the Joint with Rheumatoid Arthritis, 2001, Arthritis and Rheumatism, 44, 275-285.*
Accession No. 2003:42109, CAS Registry No. 487064-48-2, (2003).
Agosta et al., "Preparation of 3-Hydroxycyclohexaneacetonitriles", *J. Org. Chem.* 46:4880-4885 (1981).
Alcaraz et al., Preparation of Adamantane Derivatives as P2X7 Receptor Antagonists, CAS Accession No. 2001:904155.
Alcaraz et al., "Novel P2X7 Receptor Antagonists" *Bioorganic and Medicinal Chemistry Letters*, 13:4043-4046 (2003).
Author unknown, online article from www.pharmaprojects.com/therapy_analysis/purin_P2X7_0109.htm, Jan. 2009.
Baxter et al., "Hit-to-Lead Studies: The Discovery of Potent Adamantane Amide P2X7 Receptor Antagonists," *Bioorganic and Medicinal Chemistry Letters*, 13:4047-4050 (2003).
Biggs et al., "Synthesis and Pharmacological Evaluation of Some β,β-Disubstituted Analogs of Acetylcholine", *J. Med. Chem.* 15(6):642-646 (1972).
Bourrie et al., "SSR125329A, A High Affinity Receptor Ligand with Potent Anti-Inflammatory Properties," *Eur. J. of Pharm.*, 456:123-131 (2002).
Costakis et al., "Synthesis of Some Adamantane Derivatives of 2-Aminobenzothiazoles", *Journal of Medicinal Chemistry* 14(12):1222-1223 (1971).
Ferrari et al., "Extracellular ATP Triggers IL-1β Release by Activating the Purinergic P2Z Receptor of Human Macrophages", *J. Immunol.* 159:1451-1458 (1997).
Ferrari et al., "Purinergic Modulation of Interleukin-1β Release from Microglial Cells Stimulated with Bacterial Endotoxin", *J Exp. Med.* 185(3):579-582 (1997).
Fulop et al., "A Versatile Method for the Synthesis of cis-2-aminomethylcyclanols", *Synthetic Communications* 28(12):2303-2309 (1998).
Henderson et al., "Inhibition of interleukin-1-induced synovitis and articular cartilage proteoglycan loss in the rabbit knee by recombinant human interleukin-1 receptor antagonist", *Cytokine* 3(3):246-249 (1991).
Hirashima et al., "Structure-activity studies of insecticidal 2-methoxy-1,3,2-oxaza-phosphospholidine 2-sulfides against Musca domestica and Tribolium castaneum", CA 114:201707 *abstract only* of *Nippon Noyaku Gakkaishi* 15(4):539-551 (1990).
Hirashima et al., "The agonist action of substituted phenylethanolamines on octopamine receptors in cockroach ventral nerve cords", CA 118:56667 *abstract only* of *Com Biochem and Phy, Part C*: 103C(2):321-325 (1992).

(Continued)

*Primary Examiner* — Rita Desai
*Assistant Examiner* — Ben Michelson
(74) *Attorney, Agent, or Firm* — Fish & Richardson P.C.

(57) ABSTRACT

The invention provides a compound of formula (I) as defined in the specification, a process for its preparation, pharmaceutical compositions containing it, a process for preparing the pharmaceutical composition, and its use in therapy.

7 Claims, No Drawings

OTHER PUBLICATIONS

Ho et al., "Synthesis of a Peptidomimetic Tricyclic Tetrahydrobenzo[ij] quinoline as a VLA-4 Antagonist", *J. Org. Chem.* 65:6743-6748, p. 6745, scheme 5, (27) (2000).

Kadota et al., "Significance of IL-1β and IL-1 receptor antagonist (IL-1Ra) in bronchoalveolar lavage fluid (BALF) in patients with diffuse panbronchiolitis (DPB)", *Clin Exp. Immunol.* 103:461-466 (1996).

Khurana et al., "Clinical aspects of rheumatoid arthritis", Pathophysiology, vol. 12, Issue 3, Abstract (2005).

Kirkham, "Interleukin-1, Immune Activation Pathways, and Different Mechanisms in Osteoarthritis and Rheumatoid Arthritis", *Annals of the Rheumatic Diseases*, 50:395-400 (1991).

Korodi, "Nucleophilic substitution reaction of chloroquinolines with 1,2,4-triazole. II. Synthesis of 2-(1H-1,2,4-triazol-1-yl) quinolines", CA 125:275756 *abstract only* of *Het Comm* 2(3):219-226 (1996).

Leonard et al., "Small Charged Rings. II. The Synthesis of Aziridinium Salts", *J Am. Chem. Soc.* 84:4806-4813 (1962).

Li et al., "Should atherosclerosis be considered a cancer of the vascular wall?" *Medical Hypotheses*, 64:694-698 (2005).

Mackenzie et al., "Could rheumatoid arthritis have an infectious aetiology?" Drug Discovery Today: Disease Mechanism, vol. 2, Issue 3, Abstract (2005).

Miginiac et al., "Activation of Zinc by Trimethylchlorosilane: An Improved Procedure for the Preparation of β-Hydroxy Esters from Ethyl Bromoacetate and Aldehydes or Ketones (Reformatsky Reaction)", *J Org. Chem.* 52:4796-4798 (1987).

Modena et al., "Plant Growth Regulating Activities of 2-[2-(Arylamino)-2-oxoethyl]benzoic acids", *Il Farmaco* 48(4):567-572 (1993).

Otterness et al., "Possible Role of IL-1 in Arthritis: Effects of Prostaglandins in the Regulation of IL-1 Synthesis and Actions", Agent Act 39 (Suppl):109-120 (1993).

Richards et al., "Substituted 2-Phenyl-benzimidazole Derivatives: Novel Compounds that Suppress Key Markers of Allergy," Eur. J. of Medic. Chem., 41:950-969 (2006).

Sakito et al., "Interleukin 1β, Tumor Necrosis Factor Alpha, and Interleukin 8 in Bronchoalveolar Lavage Fluid of Patients with Diffuse Panbronchiolitis: A Potential Mechanism of Macrolide Therapy", *Respiration* 63:42-48 (1996).

Sharma et al., "Studies on Fused β-Lactams: Synthesis & Antibacterial Activity of Some Pyridyl/Quinolyl-2-azetidinones", *Indian Journal of Chemistry* 27B:494-497 (1988).

STN International, File REGISTRY, see RN 405068-97-5, 405070-41-9, 405076-22-4, Apr. 14, 2002.

STN International, File REGISTRY, see RN 445032-09-7, Aug. 30, 2002.

STN International, File CHEMCATS, Accession No. 2001:48444, May 14, 2001, NS18552, 2-Quinolinecarboxamide, N-(tricycle[3.3.1.13,7]dec-1-ylmethyl), CAS Registry No. 313688-07-2.

STN International, file CHEMCATS, Accession No. 2002:1977776, Jul. 9, 2002, BAS 1098675, "Cyclopropanecarboxamide, N-(2-methy1-5-quinolinyl)-", CAS Registry No. 333432-34-1.

STN International, file CHEMCATS, Accession No. Jan. 11, 2001, Cyclopropanecarboxamide, N-(2,6-dimethyl-5-quinolinyl)-(9CI)(CA Index Name), CAS Registry No. 313479-89-9.

STN International, File REGISTRY, see RN 401622-10-4, Mar. 24, 2002.

STN International, File REGISTRY, Registry Copyright Jul. 14, 2006 ACS on STN RN: 892733-99-2, 1 page.

STN International, File REGISTRY, Registry Copyright Aug. 8, 2006 ACS on STN RN: 899526-58-0, 1 page.

van den Berg, Lessons from animal models of osteoarthritis, *Curr. Opin. Rheumatol*, 13(5): 452-6 (2001).

Whitehead et al., "Diuretics. IV. 6-Chloro-3-substituted 7-Sulfamoyl-1,2,4-benzothiadiazine 1,1-Dioxides", *J. Org. Chem.* 26:2809-2813 (1961).

Yu et al., "Inhibition of IL-1 Release from Human Monocytes and Suppression of Streptococcal Cell Wall and Adjuvant-induced Arthritis in Rats by an Extract of *Tripterygium wilfordii* Hook", *Gen. Pharmac.* 25(6):1115-1122 (1994).

\* cited by examiner

QUINOLINE DERIVATIVES 057

This application claims the benefit under 35 U.S.C. §119 (e) of U.S. Provisional Application No. 60/991,265, filed on Nov. 30, 2007, which is incorporated herein by reference in its entirety.

The present invention relates to a quinoline derivative, a process for its preparation, its use in therapy, a pharmaceutical composition containing it and a process for preparing a pharmaceutical composition.

The P2X$_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the P2X$_7$ receptor by extracellular nucleotides, in particular adenosine triphosphate, leads to the release of interleukin-1β (IL-1β) and giant cell formation (macrophages/microglial cells), degranulation (mast cells) and proliferation (T cells) and apoptosis and L-selectin shedding (lymphocytes). P2X$_7$ receptors are also located on antigen-presenting cells (APC), keratinocytes, salivary acinar cells (parotid cells), hepatocytes and mesangial cells. It would be desirable to make compounds effective as P2X$_7$ receptor antagonists for use in the treatment of inflammatory, immune or cardiovascular diseases, in the aetiologies of which the P2X$_7$ receptor may play a role.

An important property for a drug acting as a P2X$_7$ receptor antagonist is that it has high potency. Moreover, it is also desirable for such drugs to possess good selectivity and pharmacokinetic properties in order to further enhance drug efficacy. As an example, it can be advantageous for such drugs to exhibit low activity against the human ether-a-go-go-related gene (hERG)-encoded potassium channel. In this regard, low activity against hERG binding in vitro is indicative of low activity in vivo.

P2X$_7$ antagonists comprising quinolinyl groups are known from WO2003/080579, WO 2004/106305, WO2005/009968 and WO2006/059945. It has now surprisingly been found that a compound generically encompassed within the class of compounds described in WO 2004/106305 exhibits advantageous pharmaceutical properties. For example, in addition to having high potency the compound of the present invention exhibits very low activity against hERG binding, enhancing its suitability for use as a pharmaceutical.

In accordance with the present invention, there is therefore provided a compound of formula (I),

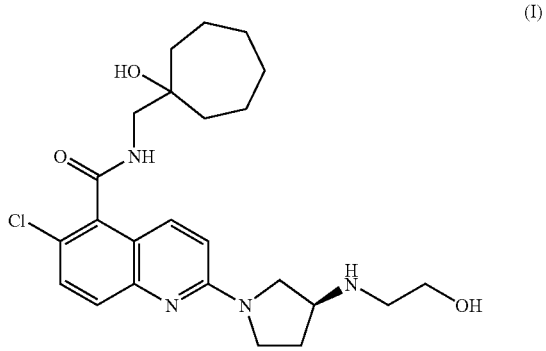

(I)

or a pharmaceutically acceptable salt thereof.

It will be understood that the compound of the present invention may exist in solvated, for example hydrated, as well as unsolvated forms. It is to be understood that the present invention encompasses all such solvated forms.

The compound of the present invention has a very high P2X$_7$ antagonist activity. In addition, it has very low affinity for the human ether-a-go-go-related gene (hERG)-encoded potassium channel and therefore is advantageous with regard to safety margins.

Pharmaceutically acceptable salts of the compound of formula (I) include, but are not limited to acid addition salts such as a hydrochloride, hydrobromide, phosphate, acetate, fumarate, maleate, tartrate, citrate, oxalate, methanesulphonate or p-toluenesulphonate salt.

The compound of the present invention comprises a chiral centre at the 3-position of the pyrrolidinyl ring (i.e. at the carbon atom to which the —NHCH$_2$CH$_2$OH substituent is directly attached). In the present invention, the stereochemical configuration at this chiral centres is (S) as designated by the Cahn-Ingold-Prelog system and as depicted in the structure of formula (I) below.

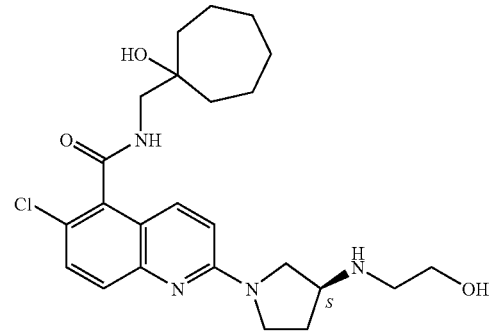

For the avoidance of doubt, the (S) stereoisomer of the present invention may be present as a mixture with the (R) stereoisomer. For example, the (S) stereoisomer may be present in a 1:1 mixture with the (R) stereoisomer.

In one embodiment, the present invention provides a compound of formula (I) that is optically pure. In the context of the present specification, the term optically pure is defined in terms of enantiomeric excess (e.e.), which is calculated from the ratio of the difference between the amounts of the respective enantiomers present and the sum of these amounts, expressed as a percentage. To illustrate, a preparation containing 95% of one enantiomer and 5% of another enantiomer has an enantiomeric excess (e.e.) of 90% [i.e. (95−5)/(95+5)× 100]. An optically pure compound according to the present invention has an e.e. of at least 90%. In an embodiment of the invention, an optically pure compound has an e.e. of at least 95%. In a further embodiment of the invention, an optically pure compound has an e.e. of at least 98%.

The chemical name of the compound of formula (I) is 6-Chloro-N-[(1-hydroxycycloheptyl)methyl]-2-{(3S)-3-[(2-hydroxyethyl)amino]-pyrrolidin-1-yl}quinoline-5-carboxamide, as determined by the IUPAC naming package of ACD Labs, Toronto, Canada.

In an embodiment of the invention, there is provided a compound which is: 6-Chloro-N-[(1-hydroxycycloheptyl) methyl]-2-{(3S)-3-[(2-hydroxyethyl)amino]-pyrrolidin-1-yl}quinoline-5-carboxamide, or a pharmaceutically acceptable salt thereof.

The compound of the present invention may be anhydrous or be in the form of a hydrate. Accordingly, one embodiment of the present invention provides a compound of formula (I) in the form of a hydrate. When in a hydrated form the water content of the compound may vary as a function of temperature or relative humidity. For example, the water content of the compound under specific conditions (e.g. given set of temperature/relative humidity) may be hemi-, mono- or dihydrated, or the water content may be non-stoichiometric. The water content of a non-stoichiometric hydrate material according to the present invention may for example be in the range of 0.1% to 8% w/w.

The present invention further provides a process for the preparation of a compound of formula (I) as defined above, or a pharmaceutically acceptable salt thereof, which comprises:
(a) reacting a compound of formula (II)

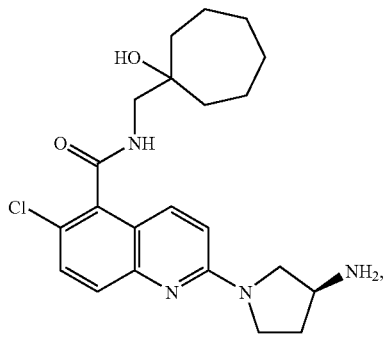

with a compound of formula (III), wherein PG represents a protecting group (e.g. silyl protecting groups such as triethylsilyl, tert-butyldimethylsilyl, benzyl ethers such as benzyl, para-methoxybenzyl, 3,4-dimethoxybenzyl and ester protecting groups such as acetate and benzoate),

under reductive amination conditions, and optionally forming a pharmaceutically acceptable salt of the compound.

The reaction of (II) and (III) may be performed in polar organic solvents such as methanol, ethanol, dichloromethane or N-methylpyrrolidine either alone or in combination with acetic acid, in the presence of a suitable reducing agent such as sodium cyanoborohydride, sodium triacetoxyborohydride or sodium borohydride. The reaction can conveniently be conducted at a temperature in the range from 0° C. to 100° C., for example at 25° C.

Compounds of formula (III) are either commercially available, are known in the literature or may be prepared using known techniques by those skilled in the art.

Compounds of formula (II) may be prepared as depicted in scheme 1.

Scheme 1

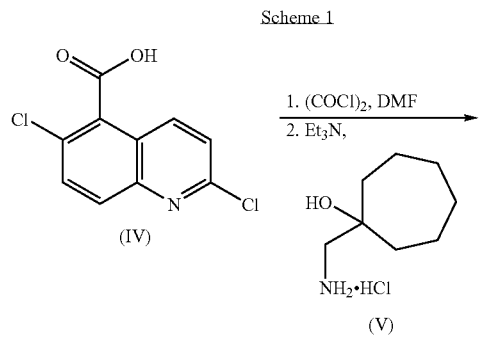

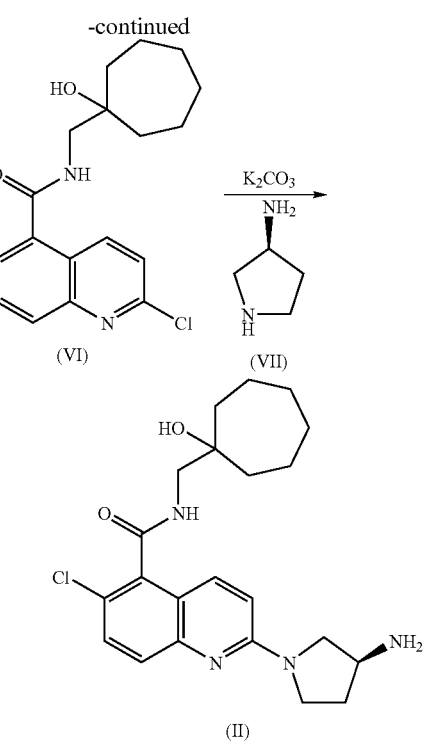

2,6-Dichloroquinoline-5-carboxylic acid (WO2004/106305) was converted to the corresponding acid chloride by treatment with oxalyl chloride and dimethylformamide in dichloromethane at room temperature. The acid chloride was then converted to amide (VI) by addition to a solution of 1-(aminomethyl)-cycloheptanol (V) (W. C. Vincek, C. S. Aldrich, R. T. Borchardt and G. L. Grunewald, J. Med. Chem., 1981, 21(1), 7-12) in dichloromethane. Amide (VI) was then reacted with (S)-3-aminopyrrolidine (VII) (Alfa Aesar, 99% ee) in refluxing acetonitrile in the presence of potassium carbonate to afford amine (II).

It will be appreciated by those skilled in the art that in the processes of the present invention certain functional groups such as hydroxyl, carboxyl or amino groups in the starting reagents or intermediate compounds may need to be protected by protecting groups. Thus, the preparation of the compounds of formula (I) may involve at a certain stage protection with and/or the removal of one or more protecting groups. The protection and deprotection of functional groups is described in 'Protective Groups in Organic Synthesis', 2nd edition, T. W. Greene and P. G. M. Wuts, Wiley-Interscience (1991) and 'Protecting Groups', P. J. Kocienski, Georg Thieme Verlag (1994). The compounds of formula (I) above may be converted to a pharmaceutically acceptable salt using conventional methods.

The compound of the present invention has beneficial potency, selectivity and pharmacokinetic properties. For example, the compound of the present invention has low affinity for the human ether-a-go-go-related-gene (hERG)-encoded potassium channel. In this regard, drugs interacting with the hERG-encoded potassium channel and consequently restoration of the negative cell potential by $K^+$ efflux, can cause a prolongation of the QT interval, leading to an acquired long QT syndrome (LQT) [M. C. Sanguinetti, C Jiang, M. E. Curran, M. T. Keating, Cell 1995, 81, 299-307; and K. Finlayson et al., Eur. J. Pharm. 2004, 500, 129-142]. This, in consequence, may induce a potentially fatal arrhythmia, known as torsade de points (TdP) [W. Haferkamp et al., Eur. Heart J. 2000, 21, 1216-1331]. New chemical entities, if not intended for cardiovascular use, which are lacking effects on cardiac channels, and the hERG channel in particular, will therefore provide an improved safety profile and so gain a therapeutic and regulatory advantage over drugs with QT prolonging effects. Kiss et al (Assay Drug Dev. Technol. 2003, 1,127-135) describe a method of assaying compounds for their ability to inhibit ion channel activity such as hERG. Springthorpe and Strandlund (WO 2005037052) describe a method of assaying compounds for their ability to bind to the IKr potassium (hERG).

The compound according to the present invention also displays acceptable oral bioavailability as determined by pharmacokinetic parameters. The compound according to the present invention also displays low plasma protein binding. The compound according to the present invention also displays low activity in an in vitro phospholipidosis screen.

The compound of the invention, or a pharmaceutically acceptable salt thereof, may be of benefit in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthropathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhocic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinophilic gastro-enteritis, mastocytosis, Crohn's disease, ulcerative colitis, microscopic colitis, indeterminate colitis, irritable bowel disorder, irritable bowel syndrome, non-inflammatory diarrhea, food-related allergies which have effects remote from the gut, e.g., migraine, rhinitis and eczema.

Accordingly, the present invention provides a compound of formula (I), or a pharmaceutically acceptable salt thereof, as hereinbefore defined for use in therapy.

In another aspect, the invention provides the use of a compound of formula (I), or a pharmaceutically acceptable salt thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

In another aspect, the invention provides compound of formula (I), or a pharmaceutically acceptable salt thereof, as hereinbefore defined for the treatment of rheumatoid arthritis.

In another aspect, the invention provides the use of a compound of formula (I), or a pharmaceutically acceptable salt thereof, as hereinbefore defined in the manufacture of a medicament for use in the treatment of rheumatoid arthritis.

In another aspect, the invention provides compound of formula (I), or a pharmaceutically acceptable salt thereof, as hereinbefore defined for the treatment of asthma or chronic obstructive pulmonary disease.

In another aspect, the invention provides the use of a compound of formula (I), or a pharmaceutically acceptable salt thereof, as hereinbefore defined, in the manufacture of a medicament for use in the treatment of asthma or chronic obstructive pulmonary disease.

In another aspect, the invention provides compound of formula (I), or a pharmaceutically acceptable salt thereof, as hereinbefore defined for the treatment of inflammatory bowel disease or Crohn's disease.

In another aspect, the invention provides the use of a compound of formula (I), or a pharmaceutically acceptable salt thereof, as hereinbefore defined in the manufacture of a medicament for use in the treatment of inflammatory bowel disease or Crohn's disease.

The invention also provides a method of treating rheumatoid arthritis, which comprises administering to a patient a therapeutically effective amount of a compound of formula (I), or a pharmaceutically acceptable salt thereof, as hereinbefore defined to a patient.

The invention also provides a method of treating an obstructive airways disease (e.g. asthma or COPD), which comprises administering to a patient a therapeutically effective amount of a compound of formula (I), or a pharmaceutically acceptable salt thereof, as hereinbefore defined to a patient.

The invention also provides a method of treating inflammatory bowel disease or Crohn's disease which comprises administering to a patient a therapeutically effective amount of a compound of formula (I), or a pharmaceutically acceptable salt thereof, as hereinbefore defined to a patient.

In order to use a compound of the invention, or a pharmaceutically acceptable salt thereof, for the therapeutic treatment of a warm-blooded animal, such as man, said ingredient is normally formulated in accordance with standard pharmaceutical practice as a pharmaceutical composition.

Therefore in another aspect the present invention provides a pharmaceutical composition which comprises a compound of the formula (I), or a pharmaceutically acceptable salt thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Cyclo-oxygenase inhibiting nitric oxide donors (CI-NODs); glucocorticosteroids (whether administered by topical, oral, intramuscular, intravenous, or intra-articular routes); methotrexate; leflunomide; hydroxychloroquine;

d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-I).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4 selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukastii, verlukast (MK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptyline or other anti-depressant agents, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor, (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1.- or B2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) capsaicin cream; (xviii) tachykinin NK1 or NK3 receptor antagonist such as NKP-608C, SB-233412 (talnetant) or D-4418; (xix) elastase inhibitor such as UT-77 or ZD-0892; (xx) induced nitric oxide synthase (iNOS) inhibitor; (xxi) chemoattractant receptor-homologous molecule expressed on TH2 cells, (such as a CRTH2 antagonist); (xxii) inhibitor of P38; (xxiii) agent modulating the function of Toll-like receptors (TLR), (xxiv) agent modulating the activity of another purinergic receptor; or (xxv) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

The invention will now be further explained by reference to the following illustrative example. In the example the NMR spectra were measured on a Varian Unity spectrometer at a proton frequency of either 300 or 400 MHz. The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® column using 0.1% aqueous trifluoroacetic acid: acetonitrile, 0.1% aqueous ammonia: acetonitrile or 0.1% ammonium acetate: acetonitrile as the eluant. Microwave reactions were performed in a CEM Discover single mode microwave. Compounds and intermediates were named by the IUPAC naming package provided by ACD Labs, Toronto, Canada.

EXAMPLE 1

6-Chloro-N-[(1-hydroxycycloheptyl)methyl]-2-{(3S)-3-[(2-hydroxyethyl)amino]-pyrrolidin-1-yl}quinoline-5-carboxamide a) 2,6-Dichloro-N-((1-hydroxycycloheptyl)methyl)quinoline-5-carboxamide

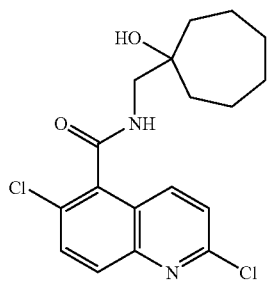

To a stirred solution of 2,6-dichloroquinoline-5-carboxylic acid (40.0 g) (WO2004/106305, Example 76, step b) under nitrogen at room temperature in dichloromethane (600 ml) was added dimethylformamide (0.13 ml) and oxalyl chloride (36.2 ml) dropwise over 2 hours in 3 portions. The mixture was then stirred at room temperature for 18 hours. The mixture was concentrated in vacuo, dichloromethane (400 ml) was added and the mixture was added dropwise to a solution of 1-(aminomethyl)cycloheptanol hydrochloride (32.7 g) (W. C. Vincek, C. S. Aldrich, R. T. Borchardt and G. L. Grunewald, J. Med. Chem., 1981, 21(1), 7-12) and triethylamine (69.1 ml) in dichloromethane (600 ml) at 0° C. over 15 minutes. The mixture was stirred for 1 hour and then water (400 ml) was added. The mixture was filtered under vacuum and the solid washed sequentially with water (2×400 ml), acetonitrile (400 ml) and diethyl ether (400 ml), then dried in vacuo to afford the subtitle product as a colourless solid (59.0 g).

m/z 367 (M+H, 100%).

1H NMR (300 MHz, CDCl₃) δ 8.24 (1H, d), 7.99 (1H, d), 7.70 (1H, d), 7.47 (1H, d), 6.52-6.42 (1H, m), 3.59 (2H, d), 1.87-1.44 (12H, m).

b) 2-[(3S)-3-Aminopyrrolidin-1-yl]-6-chloro-N-[(1-hydroxycycloheptyl)methyl]-quinoline-5-carboxamide

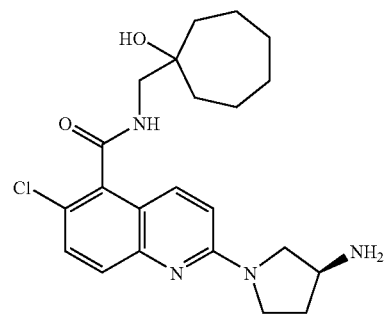

A mixture of 2,6-dichloro-N-((1-hydroxycycloheptyl)methyl)quinoline-5-carboxamide (100 g), potassium carbonate (83 g), (S)-3-aminopyrrolidine (Alfa Aesar, 99% ee) (41 ml) and acetonitrile (1 L) were heated with stirring at 82° C. under a nitrogen atmosphere for 8 hours. The mixture was then allowed to cool to room temperature, poured into water (3.3 L) and the mixture was stirred for 1 hour before being filtered and washed with water (2×300 ml), acetonitrile (200 ml) and dried in vacuo to afford the subtitle product as a pale yellow solid (94.0 g).

m/z 417 (M+H, 100%).

1H NMR (300 MHz, CDCl₃) δ 7.88 (1H, d), 7.58 (1H, d), 7.36 (1H, d), 6.69 (1H, d), 6.64 (1H, t), 3.86-3.68 (3H, m), 3.67-3.58 (1H, m), 3.53 (2H, d), 3.36-3.27 (1H, m), 2.52-2.33 (1H, m), 2.30-2.16 (1H, m), 1.94-1.18 (13H, m).

c) 2-{(3S)-3-[(2-{[tert-Butyl(dimethyl)silyl]oxy}ethyl)amino]pyrrolidin-1-yl}-6-chloro-N-[(1-hydroxycycloheptyl)methyl]quinoline-5-carboxamide

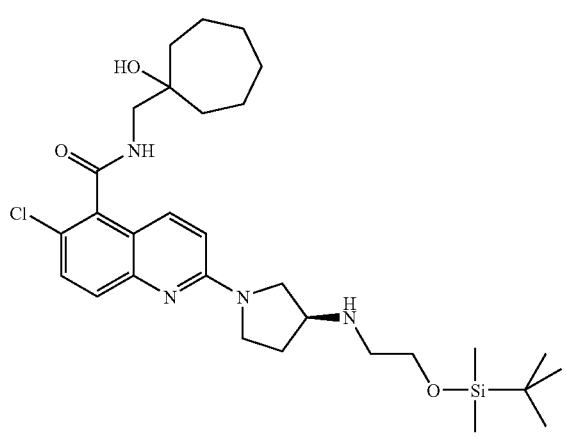

2-[(3S)-3-Aminopyrrolidin-1-yl]-6-chloro-N-[(1-hydroxycycloheptyl)methyl]-quinoline-5-carboxamide (17.6 g) was suspended in dichloromethane (300 ml) and molecular sieves (17.6 g) were added under a nitrogen atmosphere. [[(1,1-dimethylethyl)-dimethylsilyl]-oxy]acetaldehyde (7.2 ml) was added dropwise with stirring over 5 minutes and the mixture was stirred at room temperature for 6 hours. Sodium triacetoxyborohydride (17.9 g) was added in one portion and the mixture was stirred at room temperature for a further 17 hours before water (10 ml) was added, the mixture was stirred at room temperature for 30 minutes, concentrated onto silica in vacuo and purified by flash column chromatography (SiO$_2$, 1:2:97-1:8:91 7M NH$_3$ in methanol:methanol:dichloromethane as gradient elution) to afford the subtitle product as a colourless solid (16.0 g). Impure fractions (4.1 g) were repurified by flash column chromatography (SiO$_2$, 1:2:97-1:8:91 7M NH$_3$ in methanol:methanol:dichloromethane as gradient elution) to afford a second crop of the subtitle product (2.8 g).

m/z 575 (M+H, 100%).

1H NMR (300 MHz, DMSO) δ 8.40 (1H, t), 7.77 (1H, d), 7.53-7.39 (2H, m), 6.91 (1H, d), 4.17 (1H, s), 3.78-3.00 (9H, m), 2.64 (2H, t), 2.14-2.00 (1H, m), 1.83-1.72 (1H, m), 1.70-1.26 (12H, m), 0.81 (9H, d), 0.00 (6H, s).

d) 6-Chloro-N-[(1-hydroxycycloheptyl)methyl]-2-{(3S)-3-[(2-hydroxyethyl)amino]-pyrrolidin-1-yl}quinoline-5-carboxamide

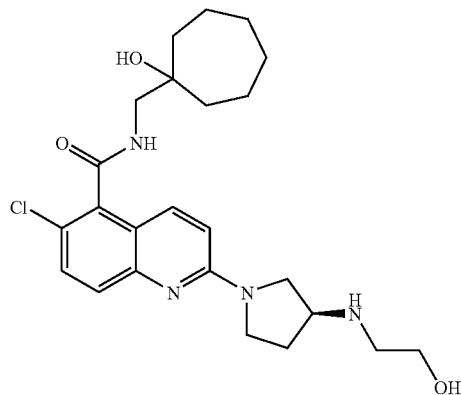

To a solution of 2-{(3S)-3-[(2-{[tert-Butyl(dimethyl)silyl]oxy}ethyl)amino]pyrrolidin-1-yl}-6-chloro-N-[(1-hydroxycycloheptyl)methyl]quinoline-5-carboxamide (26.0 g) in tetrahydrofuran (125 ml) was added hydrogen chloride (50 ml, 4M in dioxane) dropwise over ten minutes with ice bath cooling to maintain the internal temperature below 30° C. The mixture was stirred at room temperature for 2.5 hours before being concentrated in vacuo. The crude product was redissolved in MeOH (30 ml) and purified by chromatography (SiO$_2$, 1:4:95-1:10:89 7M N$_3$ in methanol:methanol:dichloromethane as gradient elution). The pure fractions were concentrated in vacuo (20.1 g) and then slurried in acetonitrile:methanol (99:1, 400 ml total volume) for 18 hours before being filtered and washed with acetonitrile (30 ml). The solid was dried in vacuo to afford the title compound as a colourless solid (18.5 g).

m.p.=138-140° C.

m/z 461 (M+H, 100%).

1H NMR (400 MHz, DMSO) 8.44 (1H, t), 7.81 (1H, d), 7.52 (1H, d), 7.48 (1H, d), 6.94 (1H, d), 3.73-3.27 (9H, m), 2.63 (2H, td), 2.15-2.05 (1H, m), 1.86-1.77 (1H, m), 1.73-1.31 (12H, m).

EXAMPLE 2

6-Chloro-N-[(1-hydroxycycloheptyl)methyl]-2-{(3S)-3-[(2-hydroxyethyl)amino]-pyrrolidin-1-yl}quinoline-5-carboxamide Hydrate

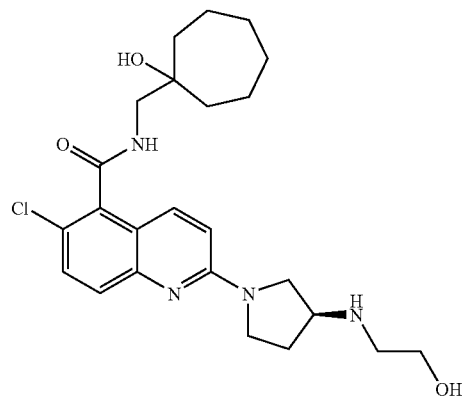

General Conditions for Example 2: NMR spectra were measured on either a Bruker Avance 360 MHz, Bruker Avance 400 MHz or a Bruker DPX250 250 MHz spectrometer.

a) 1-[(trimethylsilyl)oxy]cycloheptanecarbonitrile

Cycloheptanone (1001.0 g) and zinc iodide (10.0 g) were charged to a reaction vessel. Trimethylsilyl cyanide (1311 ml) was charged in 5 equal portions maintaining temperature at 20° C. to 25° C., and the reaction stirred for 2 hours to provide the title compound as a pale yellow oil (2049.0 g).

$^1$H NMR δ$_{CDCl3}$ 1.91-1.82 (2H, m), 1.75-1.64 (2H, m), 1.53-1.26 (8H, m), 0.00 (9H, s)

b) 1-(aminomethyl)cycloheptanol

A solution of 1-[(trimethylsilyl)oxy]cycloheptanecarbonitrile (737.5 g) in tetrahydrofuran (738 ml) was charged to a vessel containing 1 molar lithium aluminium hydride solution in tetrahydrofuran (4980 ml) and tetrahydrofuran (369 ml) whilst maintaining the temperature at 55° C. to 60° C. Tetrahydrofuran (738 ml) was charged and the reaction stirred for 3 hours at 60° C. to 65° C. The reaction was cooled to 10 to 15° C. and charged with water (193 ml), premixed sodium hydroxide solution [water (389 ml), sodium hydroxide (69 g)], tetrahydrofuran (738 ml) and water (193 ml) maintaining the temperature at 15° C. to 25° C. The mixture was stirred for 70 minutes and filtered. The filter cake was washed with tetrahydrofuran (1476 ml) twice. The filtrates and washes were combined and charged to a reaction vessel and concentrated to ca. 1480 mL at 65° C. to 70° C. The mixture was cooled to 15° C. to 25° C. and transferred to a container with tetrahydrofuran (369 ml), to provide the title compound (381 g) as a colourless solution in tetrahydrofuran (1613 ml).

$^1$H NMR δ$_{CDCl3}$ 4.61 (2H, s), 2.44 (2H, s), 1.63-1.15 (12H, m)

c) 1-(aminomethyl)cycloheptanol Hydrochloride

Acetyl chloride (264 ml) and tetrahydrofuran (191 ml) were charged to a vessel containing 2-propanol (1143 ml) maintaining the temperature at 10° C. to 15° C. 1-(aminomethyl)cycloheptanol (381 g) in tetrahydrofuran (1613 ml) and tetrahydrofuran (381 ml) were charged maintaining the temperature at 10° C. to 15° C. The reaction mixture was stirred for 50 minutes and filtered. The filter cake was washed with premixed tetrahydrofuran/2-propanol [tetrahydrofuran (267 ml), 2-propanol (114 ml)], and tetrahydrofuran (1905 ml). The filter cake was dried at 40° C. for 23 hours to provide the title compound as a colourless solid (464 g).

$^1$H NMR $\delta_{CD3OD}$ 4.97 (3H, s), 2.91 (2H, s), 1.80-1.48 (12H, m).

c) 2,6-Dichloro-N-((1-hydroxycycloheptyl)methyl)quinoline-5-carboxamide

Thionyl chloride (249 ml) and toluene (276 ml) were charged to a vessel containing 2,6-dichloroquinoline-5-carboxylic acid (276.0 g) and toluene (2760 ml). The reaction mixture was stirred at 80° C. to 85° C. for 3 hours. The reaction mixture was concentrated to ca. 1380 mL at 30° C. to 40° C. Toluene (2760 ml) was charged and the mixture concentrated to ca. 1380 mL at 30° C. to 40° C. Toluene (828 ml) was charged, and the resulting solution and toluene (276 ml) were charged to a reaction vessel containing 1-(aminomethyl)cycloheptanol hydrochloride (205 g), triethylamine (491 ml) and toluene (1930 ml) at 0° C. to 10° C. The reaction was stirred for 1 hour at 0° C. to 5° C., then 2 hours at 20° C. to 25° C. Water (2200 ml) was charged the mixture stirred for 40 minutes and filtered. The filter cake was washed with water (1100 ml) twice, toluene (1380 ml), water (1100 ml) and toluene (1380 ml). The filter cake was dried at 40° C. for 41 hours to provide the title compound as an off white solid (375.76 g). $^1$H NMR $\delta_{DMSO}$ 8.65 (1H, t), 8.24 (1H, d), 8.01 (1H, d), 7.89 (1H, d), 7.72 (1H, d), 4.27 (1H, s), 3.36 (2H, d), 1.74-1.32 (12H, m)

e) 2-[(3S)-3-Aminopyrrolidin-1-yl]-6-chloro-N-[(1-hydroxycycloheptyl)methyl]-quinoline-5-carboxamide (S)-3 aminopyrrolidine (96 ml) and acetonitrile (300 ml) were charged to a vessel containing 2,6-Dichloro-N-((1-hydroxycycloheptyl)methyl)quinoline-5-carboxamide (300.0 g), potassium carbonate (249.0 g) and acetonitrile (2400 ml). The reaction mixture was heated under reflux for 20 hours. Water (6900 ml) was charged at 20° C. to 25° C. The mixture was stirred for 95 minutes and filtered. The filter cake was washed with water (1200 ml) and acetonitrile (1200 ml). The filter cake was dried at 40° C. for 48 hours to provide the title compound as a yellow solid (283 g).

$^1$H NMR $\delta_{DMSO}$ 8.45 (1H, t), 7.82 (1H, d), 7.56-7.46 (2H, m), 6.95 (1H, d), 4.21 (1H, s), 3.71-3.48 (4H, m), 3.36-3.23 (3H, m), 2.15-2.06 (1H, m), 1.83-1.32 (13H, m).

f) 2-{(3S)-3-[(2-{[tert-Butyl(dimethyl)silyl]oxy}ethyl)amino]pyrrolidin-1-yl}-6-chloro-N-[(1-hydroxycycloheptyl)methyl]quinoline-5-carboxamide

[[(1,1-dimethylethyl)-dimethylsilyl]-oxy]acetaldehyde (66.3 g) and tetrahydrofuran (150 ml) were charged to a vessel containing 2-[(3S)-3-Aminopyrrolidin-1-yl]-6-chloro-N-[(1-hydroxycycloheptyl)methyl)]quinoline-5-carboxamide (158.7 g), magnesium sulfate (75.0 g), sodium triacetoxyborohydride (175.5 g) and tetrahydrofuran (1350 ml) at 15° C. to 25° C. The reaction mixture was stirred for 20 hours and premixed sodium hydrogen carbonate solution [water (730 ml), sodium hydrogen carbonate (72.2 g)], was charged. Mixed heptanes (150 ml) was charged and the mixture stirred for 90 minutes and the layers were separated. The organic layer was recharged to the vessel with premixed sodium hydrogen carbonate solution [water (730.3 ml), sodium hydrogen carbonate (72.2 g)] and stirred for 30 minutes before separating the layers. The organic layer was washed with water (750 ml) and recharged to the reaction vessel. Tetrahydrofuran (1500 ml) was charged and the mixture was concentrated to ca. 1500 mL at 40° C. to 45° C. Tetrahydrofuran (1500 mL) was charged and the mixture was concentrated to ca. 1500 mL at 40° C. to 45° C. and filtered. The filter cake was washed with tetrahydrofuran (150 ml) and to the filtrate and wash were combined and charged to a reaction vessel, Heptanes (1500 ml) was charged and the mixture concentrated to ca. 1500 mL at 40° C. to 50° C. Heptanes (1500 ml) was charged and the mixture concentrated to ca. 1500 mL at 40° C. to 50° C. The mixture was cooled to 15° C. to 20° C., stirred for 75 minutes and filtered. The filter cake was washed with heptanes (300 ml) and dried on the filter to provide the crude title compound as a pale yellow solid (182.8 g).

The crude title product (170 g) was charged to a reaction vessel with methanol (170 ml) and 2-propanol (510 ml). The mixture was warmed to 40° C. to 45° C. and stirred for 40 minutes. The mixture was cooled to 18° C. to 23° C. and stirred for 2.5 hours. The mixture was cooled to 0 to 5° C., stirred for 1 hour and filtered. The filter cake was washed with premixed methanol/2-propanol [methanol (85 ml), 2-propanol (255 ml)] and dried at 40° C. to provide the title compound as an off-white solid (124 g).

$^1$H NMR $\delta_{DMSO}$ 8.40 (1H, t), 7.77 (1H, d), 7.53-7.39 (2H, m), 6.91 (1H, d), 4.17 (1H, s), 3.78-3.00 (9H, n), 2.64 (2H, t), 2.14-2.00 (1H, m), 1.83-1.72 (1H, m), 1.70-1.26 (12H, m), 0.81 (9H, d), 0.00 (6H, s).

g) 6-Chloro-N-[(1-hydroxycycloheptyl)methyl]-2-{(3S)-3-[(2-hydroxyethyl)amino]-pyrrolidin-1-yl}quinoline-5-carboxamide Hydrate Premixed hydrochloric acid solution [cHCl (516.0 g), water (4813 ml)] was charged to a reaction vessel containing 2-{(3S)-3-[(2-{[tert butyl(dimethyl)silyl]oxy}ethyl)amino]pyrrolidin-1-yl}-6-chloro-N-[(1-hydroxycycloheptyl)methyl]quinoline-5-carboxamide (525.0 g) and toluene (5250 ml) at 20° C. to 30° C. The reaction mixture was stirred at 25° C. to 30° C. for 20 hours and filtered. The filter cake was washed with water (525 ml). The filtrate and wash were combined and the layers were separated. The aqueous layer was washed with toluene (2625 ml), and charged to a reaction vessel. Premixed potassium bicarbonate solution [water (1803 ml), potassium bicarbonate (601.3 g)] and n-butanol (5250 ml) were charged at 25° C. to 30° C. and the resulting mixture stirred for 67 minutes. The phases were separated and the aqueous phase extracted with n-butanol (2625 ml). The combined butanol phases were combined and washed with water (2600.0 ml) four times. At this point the butanol solution was combined with the butanol solution from a reaction of identical scale. The solution was filtered and the filter cake washed with n-butanol (1050 ml). The filtrate and wash were combined and concentrated to ca. 9.5 L at 40° C. to 50° C. n-Butanol (1050 ml) was charged and concentrated to ca. 9.5 L at 40° C. to 50° C. n-Butanol (1050 ml) was charged and concentrated to ca. 10.5 L at 40° C. to 50° C. n-Butanol (1050 ml) was charged and concentrated to ca. 10.5 L at 40° C. to 50° C. n-Butanol (1050 ml) was charged and concentrated to ca. 10.5 L at 40° C. to 50° C. The mixture was concentrated to ca 5.3 L at 40° C. to 50° C. The mixture was held at 40° C. to 50° C. for 61 hours and mixed heptanes (5250 ml) were charged at 40° C. to 50° C. The mixture was stirred at 40° C. to 50° C. for 60 minutes, at 20 to 25° C. for 92 minutes and filtered. The filter cake was washed with premixed heptanes and n-butanol [heptanes (2100 ml) n-butanol (2100 ml)]. The filter cake was dried at 40° C. for 30 hours, at 60° C. for 24 hours, at 65° C. for 19 hours and 80° C. for 9 hours to provide the title compound as an off-white solid (524.4 g).

$^1$H NMR $\delta_{dmso}$ 8.44 (1H, t), 7.81 (1H, d), 7.52 (1H, d), 7.48 (1H, d), 6.94 (1H, d), 3.73-3.27 (9H, m), 2.63 (2H, td), 2.15-2.05 (1H, m), 1.86-1.77 (1H, m), 1.73-1.31 (12H, m).

To obtain a consistent hydrated form the 2-{(3S)-3-[(2-{[tert-butyl(dimethyl)silyl]oxy}ethyl)amino]pyrrolidin-1-yl}-6-chloro-N-[(1-hydroxycycloheptyl)methyl]quinoline-5-carboxamide obtained was further processed as follows. A hastelloy vessel was charged with 6-Chloro-N-[(1-hydroxycycloheptyl)methyl]-2-{(3S)-3-[(2-hydroxyethyl)amino]-pyrrolidin-1-yl}quinoline-5-carboxamide (40 g, 1 wt), toluene (7.0 vol, 280 mL) and water (11.2 mL, 7.0 eq.) and the contents heated to 45 to 50° C. and stirred at this temperature for 22 hours. The mixture was then cooled to 18 to 23° C. over 1 hour and then aged at 18 to 23° C. for a further hour before filtering under a nitrogen flow and vacuum. Filtration took 6 minutes. The cake was washed with a mixture of toluene (80 mL, 2.0 vol) and water (3.2 mL, 0.08 vol.) and was dried on the filter for 30 minutes under nitrogen flow before removal. The product was isolated as a pale yellow solid 46.7 g. A portion of wet material (35.2 g) was dried under vacuum at 18 to 23° C. for 72 hours to give 30.2 g of the title compound (100% recovery, pro-rata). The water content of the product was determined to be 1.7% w/w by Karl Fischer titration using a Mitsubishi CA-20 (Predicta OM-1000) moisture meter.

Pharmacological Analysis

P2X$_7$ Assay

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p. 126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, the compound of the invention was tested for antagonist activity at the P2X$_7$ receptor. Thus, the test was performed in 96-well flat bottomed microtitre plates, the wells being filled with 250 µl of test solution comprising 200 µl of a suspension of THP-1 cells (2.5×10$^6$ cells/ml) containing 10$^{-4}$M ethidium bromide, 25 µl of a high potassium buffer solution containing 10$^{-5}$M bbATP, and 25 µl of the high potassium buffer solution containing concentrations of test compound typically from 30 µM-0.001 µM. The plate was covered with a plastic sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ FIGURE was calculated, this FIGURE being the negative logarithm of the concentration of test compound necessary to reduce the bbATP agonist activity by 50%.

hERG Binding Protocol

The hERG assay was performed according to the procedure described in WO2005/037052. The affinity (pIC$_{50}$) of compounds for the ion channel subunit encoded by the human ether-a-go-go-related gene (hERG) gene was determined by competition binding of radioligand 3,7-Bis[2-(4-nitro [3,5-$^3$H]phenyl)ethyl]-3,7-diazabicyclo[3.3.1]nonane to HEK (human embryonic kidney) cell membranes expressing hERG, in a filter wash format.

Membranes were incubated for 3 hours at room temperature with serial dilutions of the test compounds, radioligand 3,7-Bis[2-(4-nitro[3, 5-3H]phenyl)ethyl]-3,7-diazabicyclo [3.3.1]nonane at 1 nM final concentration, and assay buffer (10 mM HEPES, 130 mM NaCl, 5 mM KCl, 1 mM EGTA, 0.8 mM MgCl$_2$, pH 7.4). The assay was conducted in a final volume of 200 µL, in the presence of 1% (v/v) dimethyl sulphoxide. Non-specific binding was determined by measuring the binding of 3,7-Bis[2-(4-nitro[3,5-$^3$H]phenyl)ethyl]-3, 7-diazabicyclo[3.3.1]nonane in the presence of 10 µM astemizole. During this incubation GF/B filter plates were immersed in coating solution 0.3% (v/v) Polyethylenimine and 0.2% (w/v) BSA). Following incubation assay plates were harvested onto precoated GF/B filter plates using a Tomtec harvester.

The pIC$_{50}$, defined as the negative logarithm of the concentration of compound required for 50% reduction in 3,7-Bis[2-(4-nitro[3,5-$^3$H]phenyl)ethyl]-3,7-diazabicyclo[3.3.1] nonane binding, was determined. A 'less than' FIGURE indicates <50% inhibition at the quoted concentration, this being the highest concentration tested.

Results of P2X$_7$ Assay and hERG Binding Protocol

The compound of the invention demonstrated very high P2X$_7$ antagonist activity, having a pIC$_{50}$ FIGURE of 8.4. Moreover, the compound displayed particularly low hERG activity, with less than 50% inhibition at the highest concentration tested. Table 1 shows P2X$_7$ pIC$_{50}$ values and hERG pIC$_{50}$ values for the compound of the invention and comparative compounds exemplified in WO 2004/106305 (Examples 29, 36, 44 and 50).

TABLE 1

| Example Number | P2X$_7$ pIC$_{50}$ | hERG pIC$_{50}$ | P2X$_7$:hERG Ratio |
|---|---|---|---|
| 1 | 8.4 | <4 | >20,000 |
| 29 WO 2004/106305 | 7.2 | 4.5 | 502 |
| 36 WO 2004/106305 | 8.2 | 5.1 | 1258 |
| 44 WO 2004/106305 | 7.9 | 4.9 | 1000 |
| 50 WO 2004/106305 | 7.5 | 4.9 | 398 |

The compound according to the present invention registered a P2X$_7$ IC$_{50}$ value at concentrations of 5 nM or lower. Further, it did not display sufficient activity to register an IC$_{50}$ for hERG at a concentration of 100 µM. Accordingly, the compound of the present invention has a ratio of P2X$_7$:hERG affinity of >20,000. The comparative compounds, Examples 29, 36, 44 and 50 of WO 2004/106305, respectively registered a hERG IC$_{50}$ at a concentration of 32 µM, 8 µM, 13 µM and 13 µM and required a concentration of 63 nM, 6 nM, 13 nM and 32 nM to register a P2X$_7$ IC$_{50}$. Accordingly, their P2X$_7$: hERG affinity ratios are just 502, 1258, 1000 and 398 respectively.

Bioavailability—Rat PK

Pharmacokinetic parameters and concepts are used in DMPK to describe the fate of a compound in the body. The distribution and excretion of a compound are reflected in the plasma concentration-time profile. By appropriate dosing, sampling and analysis key as parameters (clearance, volume, half-life, bioavailability etc.) can be determined.

Test compounds were typically dosed intravenously to the right lateral tail vein of male Sprague Dawley rats at a dose level of 3 mg/kg (1 ml/kg) in DMA:water (40:60 v/v). Rats were dosed orally at a dose level of 5 mg/kg (2 ml/kg) in 0.5% hydroxypropylmethylcellulose (HPMC, w/v)/0.1% Tween 80 (v/v) in water). Following IV administration, serial blood samples (200 µl) were taken from the left lateral tail vein at 2, 4, 8, 15, 30, 60, 120, 180, 300, 420, 720 and 1440 nm in and at 0, 20, 40, 60, 120, 180, 300, 420, 720 and 1440 min following oral administration. Plasma was prepared by centrifugation.

To determine the plasma levels of test compound, 50 µl of methanol was added to 50 µl of each of the test samples, whilst 40 µl of methanol was added to the 50 µl aliquots of control plasma containing 10 µl spikes of authentic standard used to create a calibration line and QCs. Finally, 100 µl of methanol containing a chemically similar internal standard was added to each sample, standard and QC giving a final volume of 200 µl. All plasma samples were then thoroughly mixed and placed at −20° C. for at least an hour prior to centrifugation. The resultant supernatants were analysed by HPLC-MSMS after an appropriate, selective and sensitive method had been created by optimizing both cone voltage and collision energy.

Pharmacokinetic parameters were derived from concentration-time using non-compartmental analysis in WinNonLin®. Bioavailability was calculated using the following equation $F=AUC_{PO}*Dose_{IV}/AUC_{IV}*Dose_{PO}$.

The compound according to the present invention registered the following pharmacokinetic data: Rat po Bioavailability=14%

In Vitro Phospholipidosis Protocol

Assessment of a compounds potential to induce phospholipidosis was determined by an in vitro fluorescent assay which reports the accumulation of phospholipids in primary rat hepatocytes. Hepatocytes were isolated from Han Wistar rats by a 2-stage collagenase digest method. The hepatocytes were then plated on collagen coated 96-well plates in William's E medium. The cells were left to adhere for 1 hour then the media was replaced with a solution of 250 µg.ml$^{-1}$ collagen in Hepatozyme cell culture medium.

Cells were then cultured for 48 hours with the medium being changed at 24 hours. At 48 hours post isolation the medium was changed to Hepatozyme supplemented with the fluorescent phospholipid N-(6-tetramethylrhodaminethiocarbamoyl)-1,2-dihexadecanoyl-sn-glycero-3-phosphoethanolamine (DHPE-TRITC) (5 µg.ml$^{-1}$). At this time, test compounds were added to the hepatocytes at a range of concentrations in a serial dilution with a final concentration of 0.4% dimethylsulfoxide (used as solvent for test compounds).

The cells were incubated for a further 24 hours and then fixed by addition of a phosphate buffered saline (PBS) solution containing the nuclear stain Hoechst 33342 (final concentration 2 µM) and paraformaldehyde solution (final concentration 4%). The plates were kept at room temperature for 30 minutes then washed three times in PBS solution.

Images of the hepatocytes were then acquired using an automated microscope platform (GE In Cell Analyser 3000). Image analysis algorithms were then used to assess cell viability and the accumulation of the DHPE-TRITC label within viable hepatocytes. The quantified accumulation observed with test compounds was then normalised to a range of 0, representing the accumulation observed in cells exposed to vehicle only, and 1, representing cells exposed to 10 µM amiodarone. The maximum accumulation across the dose response of the test compound, where cell viability is >50%, is reported, as is the dose at which this maximum was observed. The lowest dose that caused >50% cell toxicity is also reported. Toxicity in individual cells is identified as a change in nuclear labelling to a condensed, punctuate morphology.

The dose at which phospholipidosis is observed is known to be inversely correlated with the in vivo incidence of phospholipidosis (David K Monteith, Ryan E Morgan & Bartley Halstead (2006) "In vitro assays and biomarkers for drug-induced phospholipidosis". Expert Opinion on Drug Metabolism & Toxicology, vol. 2 (5), pp 687-696).

The compound according to the present invention registered a maximum accumulation of 0.9 (relative to 10 µM amiodarone control) at a maximum accumulation concentration of 71 µM. Further, it registered a minimum toxic concentration of 198 µM. By comparison Example 44 of WO2004/106305 registered a maximum accumulation of 0.6 at a maximum accumulation concentration of 8 µM and a minimum toxic concentration of 23 µM.

Measurement of Plasma Protein Binding

The extent of plasma protein binding was determined via equilibrium dialysis of a compound between human plasma and aqueous buffer at 37° C., and determination of the concentrations of compound in the plasma and buffer by HPLC-MS/MS.

Dialysis cells (molecular weight cut-off 5000) were prepared by rinsing with water followed by soaking in the dialysis buffer for a minimum of 1 hour. The dialysis buffer was isotonic buffered saline pH 7.4. Stock solutions of compound in dimethylsulfoxide were prepared at a concentration of 0.5 mM.

The stock DMSO solution of compound was added to the plasma at a ratio of 10 µl of DMSO to each ml of plasma. This gave a 1% DMSO in plasma solution with each compound at a concentration of 5 µM.

Dialysis cells were then prepared and one half of the cell filled with 750 µl of dialysis buffer and the other half of the cell with 750 µl of plasma solution of compound. Once prepared the cells were sealed and placed in an incubator box at 37° C. These cells were then rotated for a minimum of 4 hours to equilibrate.

After equilibration 500 µl of the buffer samples were removed and added to HPLC vials along with 100 µl of plasma (sample in 6-fold diluted plasma), and 100 µl of the plasma samples were removed and added to HPLC vials along with 500 µl of dialysis buffer (sample in 6-fold diluted plasma).

The samples were then analysed using HPLC-MS/MS. A four point calibration curve was obtained by dilutions of the stock solutions with 6-fold diluted plasma at concentrations of 0.013 µM, 0.05 µM, 0.25 µM and 1.25 µM which were injected in this order followed by the buffer sample and then the plasma sample.

Calculation

The concentration of compound in the samples were determined using MassLynx version 4.1 software (produced by Waters/Micromass) that automatically calculated a calibration curve and interpolated the concentration of compound in the analytes. Plasma protein binding was determined from the measured concentration as the percentage of compound bound in plasma (% bound) using the following equation;

$$\% \text{ bound} = 100 - 100\left(\frac{1.05(6*\text{plasma }conc - 1.2*\text{buffer }conc)}{1.05\left(\begin{array}{c}6*\text{plasma }conc - \\ 1.2*\text{buffer}\cdot conc\end{array}\right) + 1.2*\text{buffer }conc}\right)$$

The compound according to the present invention registered a human plasma protein binding (% bound) of 70%.

The invention claimed is:

1. A compound of formula (I)

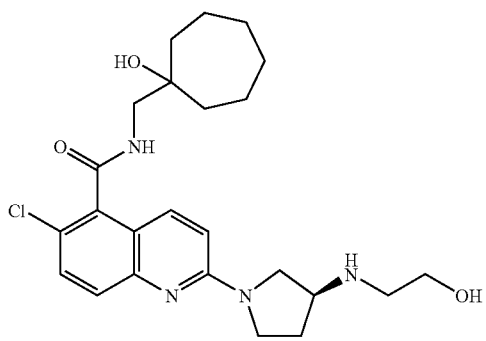

or a pharmaceutically acceptable salt thereof.

2. A pharmaceutical composition comprising a compound of formula (I), or a pharmaceutically acceptable salt thereof, as claimed in claim 1 and a pharmaceutically acceptable adjuvant, diluent or carrier.

3. A process for the preparation of a pharmaceutical composition comprising a compound of formula (I), or a pharmaceutically acceptable salt thereof, as claimed in claim 1 and a pharmaceutically acceptable adjuvant, diluent or carrier, which process comprises mixing the compound of formula (I), or the pharmaceutically acceptable salt thereof, with the pharmaceutically acceptable adjuvant, diluent or carrier.

4. A method of treating rheumatoid arthritis, which comprises administering a therapeutically effective amount of a compound of formula (I), or a pharmaceutically acceptable salt thereof, as claimed in claim 1 to a patient in need thereof.

5. A method of treating inflammatory bowel disease or Crohn's disease, which comprises administering a therapeutically effective amount of a compound of formula (I), or a pharmaceutically acceptable salt thereof, as claimed in claim 1 to a patient in need thereof.

6. A process of preparing a compound of formula (I) as defined in claim 1, which comprises reacting a compound of formula (II)

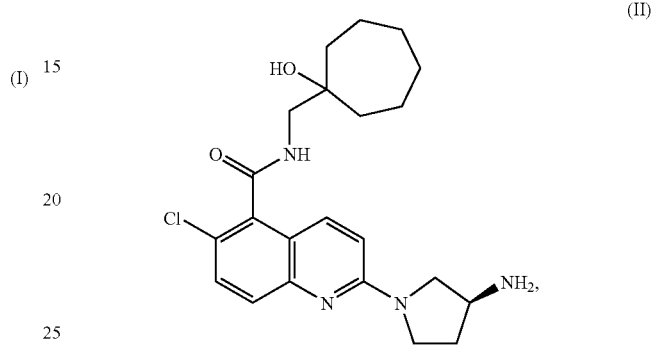

with a compound of formula (III), wherein PG represents a protecting group,

under reductive amination conditions,
and optionally forming a pharmaceutically acceptable salt of the compound.

7. A compound according to claim 1, wherein the compound of formula (I) is in the form of a hydrate.

* * * * *